great Britain

United States Patent [19]
Dove et al.

[11] Patent Number: 5,366,455
[45] Date of Patent: Nov. 22, 1994

[54] PEDICLE ENGAGING MEANS

[75] Inventors: John Dove, Staffs; Abdul A. Rahmatalla, Harpfields; Philip J. Sell, Sutton Coldfield, all of Great Britain

[73] Assignee: Surgicraft Limited, Worcs., England

[21] Appl. No.: 536,589

[22] PCT Filed: Nov. 2, 1989

[86] PCT No.: PCT/GB89/01013
§ 371 Date: Feb. 19, 1991
§ 102(e) Date: Feb. 19, 1991

[87] PCT Pub. No.: WO90/04948
PCT Pub. Date: May 17, 1990

[30] Foreign Application Priority Data
Nov. 4, 1988 [GB] United Kingdom ............ 8825909.8

[51] Int. Cl.⁵ .................................................. A61B 17/00
[52] U.S. Cl. ........................................ 606/61; 606/60; 606/69
[58] Field of Search ............... 606/53, 60, 61, 72, 606/73, 69; 623/16, 17; 128/69; 403/385, 389, 390, 391, 395, 396

[56] References Cited
U.S. PATENT DOCUMENTS

| | | | |
|---|---|---|---|
| 1,798,223 | 3/1931 | Richardson | 403/391 |
| 2,349,648 | 5/1944 | Brickman | 403/391 X |
| 2,422,332 | 6/1947 | Becker | 403/351 X |
| 2,426,857 | 9/1947 | Birkenmaier | 403/390 X |
| 3,779,240 | 12/1973 | Kondo | 606/69 |
| 4,219,015 | 8/1980 | Steinemann | 606/69 |
| 4,289,123 | 9/1981 | Dunn | 623/17 X |
| 4,592,279 | 6/1986 | Kemmerer | 403/389 X |
| 4,641,636 | 2/1987 | Cotrel | 606/61 |
| 4,696,290 | 9/1987 | Steffee | 606/61 |
| 4,738,251 | 4/1988 | Plaza | 606/61 |
| 4,998,936 | 3/1991 | Mehdian | 606/61 |

Primary Examiner—Robert A. Hafer
Assistant Examiner—Brian E. Hanlon
Attorney, Agent, or Firm—Trexler, Bushnell, Giangiorgi & Blackstone, Ltd.

[57] ABSTRACT

Pedicle engaging device having a bridge member (10) and two clip members (15); the bridge member having an arched middle portion (11) with concave edges (22) to afford clearance with respect to adjacent spinous processes (23), an aperture (12) in each side of the arch, and a pair of end portions (13) each with a hole for a pedicle screw (29); each clip member (15) having a tip (16) engageable in one of the apertures (12), and a fixing portion (17) with a hole (18) for receiving a pedicle screw (29); and each clip member being cranked (at 19) so as to form with the junction (20) between the arch (11) and respective end portion (13) of the bridge member (10) a pair of clamping parts for embracing a rod or rod-like portion (21') of a spinal fixation device (26).

5 Claims, 3 Drawing Sheets

PEDICLE ENGAGING MEANS

This invention relates to pedicle engaging means for use in spinal surgery.

Pedicle screws are well known for use in systems for internal fixation of the spine. However, problems have arisen in attempting to use pedicle screws in systems for segmental spinal fixation. Some pedicle screws need wires to secure them to rods or other devices used for segmental spinal fixation. An alternative which is sometimes used is to make use of plates (instead of rods) or custom built devices. Pedicle screws may be used when there is no lamina present and when consequently methods of sub-lamina wiring are unsuitable.

The object of the present invention is to provide pedicle engaging means particularly suited to use with existing segmental spinal fixation devices such as "Luque rods" or, more particularly, "Hartshill Rectangles" for posterior spinal surgery.

According to the present invention, pedicle engaging means comprises a bridge member having an arched middle portion with an aperture in each side of the arch, and a pair of generally coplanar end portions each with a hole for rotatably receiving a pedicle screw; and a pair of clip members each having a tip engageable in one aperture in the arched portion of the bridge member, and each having a fixing portion with a hole for rotatably receiving a pedicle screw; the hole in a clip member being in register with the hole in the respective end portion of the bridge member when the tip of the clip member is engaged in the respective aperture in the arched portion of the bridge member, and the portion of the clip member between its tip and its fixing portion being cranked so as to form with the junction between the arched portion and the respective end portion of the bridge member a pair of clamping parts for embracing a rod or rod-like portion of a spinal fixation device.

It is anticipated at present that there are three likely occasions when the pedicle engaging means of the invention will be used:
1. When there has been a previous extensive wired laminectomy in the lumbar region.
2. When it is necessary to bridge a number of levels and to engage intervening levels particularly to reduce slip in spondylolisthesis.
3. In painful spondylolysis in young patients where at present with sublaminar wiring the level above has to be included in order to gain fixation, whereas with the pedicle engaging means of the invention the internal fixation can be limited to one motion segment.

The bridge member and the two clip members may be formed of any biocompatible material, but a flexible material, such as stainless steel strip, enables the shape of the arched portion to be modified by the surgeons to vary the spacing between the screw holes and/or the alignment of or angularity between the end portions containing the screw holes. However, more than one size of bridge member may be provided, with arched portions of different span and/or height. The width of the arched portion may be reduced between the apertures for engagement by the tips of the clip members, e.g., the edges of the arched portion may be concave in plan view to form a neck having its least width at the middle, to afford clearance with respect to adjacent spinous processes.

The holes in the end portions of the bridge member and/or the holes in the fixing portions of the clip members may be elongated in the lengthwise direction of the bridge member, to allow adjustment of the spacing and/or inclination of pedicle screws with respect to the general plane of the end portions of the bridge member. Formation and elongation of the holes may be effected by means of a ball cutter applied to the remote faces of the end portions of the bridge member and the fixing portions of the clip members respectively and moved towards the arched portion of the bridge member and away from the tips of the clip members respectively.

An embodiment of the invention, and the manner of its use, will now be described, by way of example only, with reference to the accompanying drawings, in which.

Figure 1:
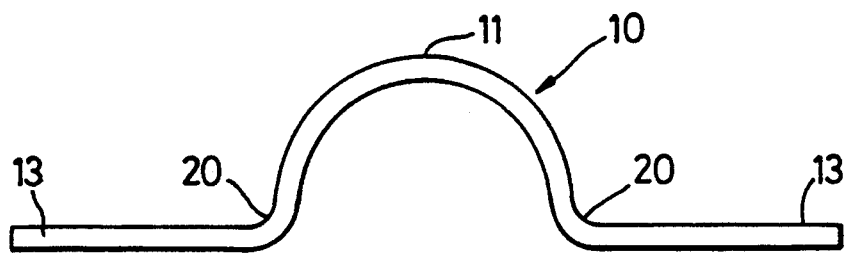
FIG. 1 is a side elevation of the bridge member of pedicle engaging means in accordance with the invention.
Figure 7:
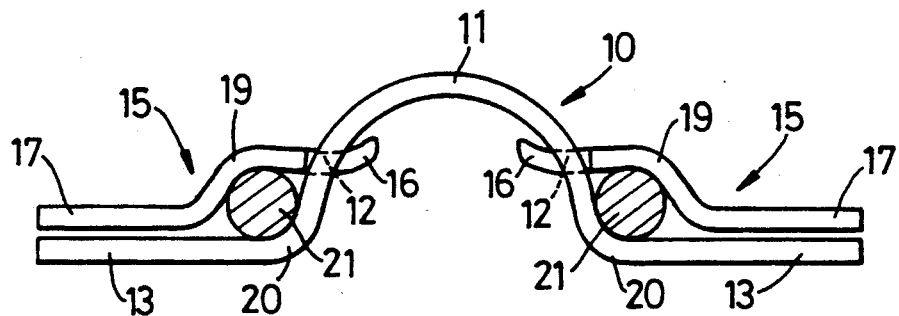
Figure 8:
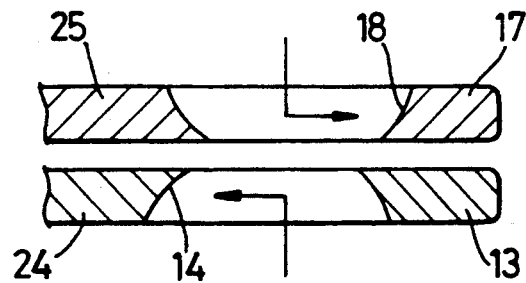
Figure 9:
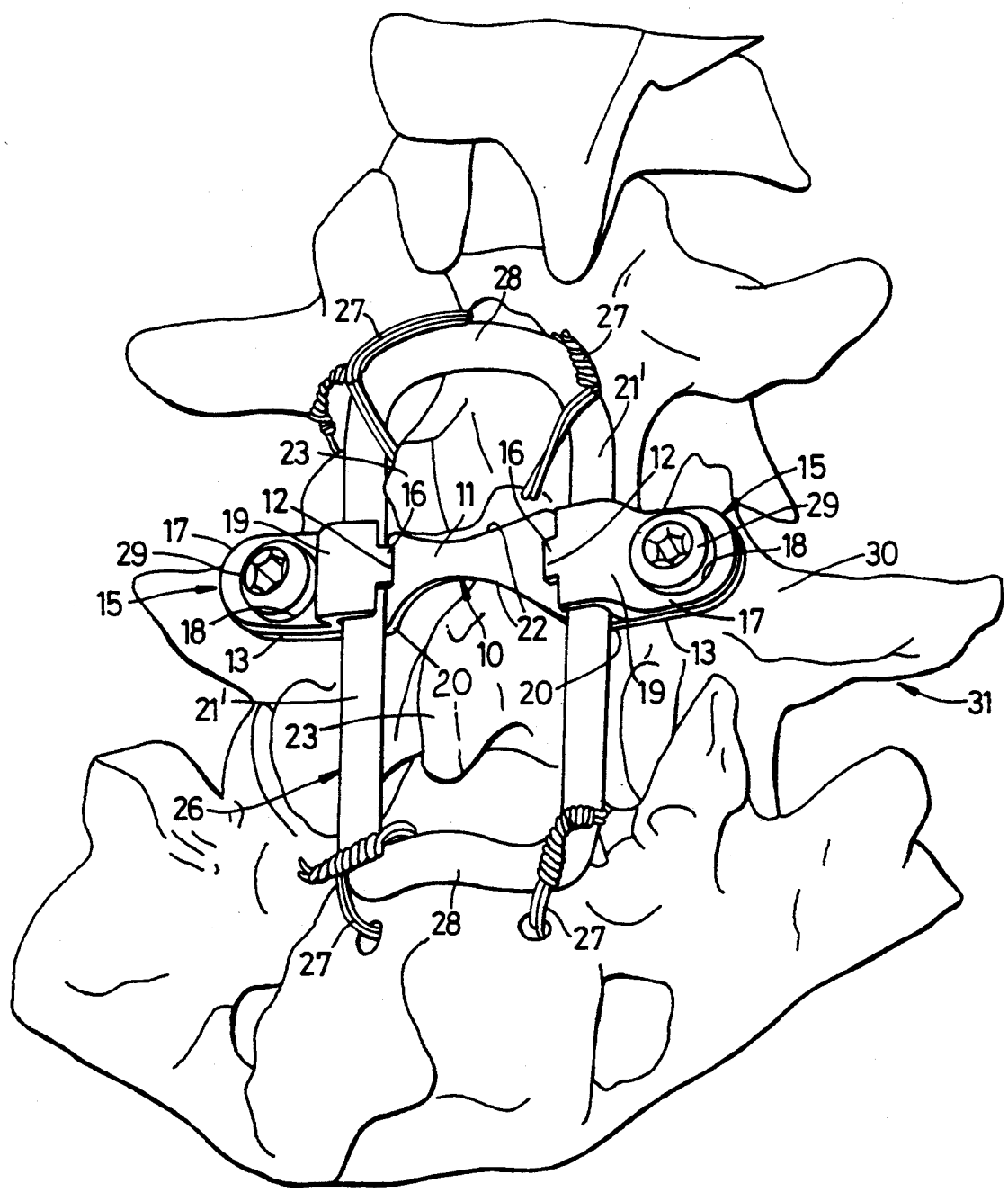

FIG. 7 corresponds to FIG. 1 but shows the clip members engaged with the bridge member and rods in place for clamping thereto;

FIG. 8 is an enlarged fragmentary section through the right hand end portion of the bridge member and the fixing portion of the corresponding clip member, and indicating the manner of elongating the holes; and FIG. 9 is a perspective view showing the assembly of bridge member and clip members clamped to a "Hartshill Rectangle" and secured by pedicle screws.

Figure 2:
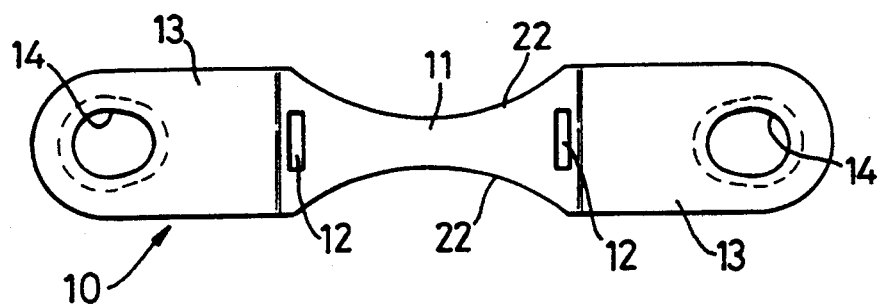
FIG. 2 is a plan of the bridge member.
Figure 3:
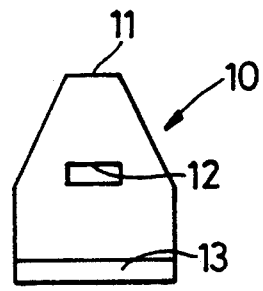
FIG. 3 is an end elevation of the bridge member.

In FIGS. 1 to 3 a bridge member 10 for pedicle engaging means in accordance with the invention has an arched middle portion 11 with an aperture 12 in each side of the arch, and a pair of generally coplanar end portions 13 each with a hole 14 for rotatably receiving a pedicle screw (see FIG. 9).

Figure 4:
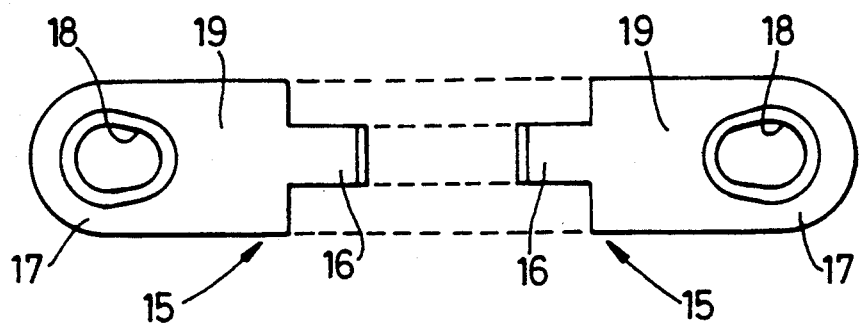
FIG. 4 is a plan view illustrating a method of simultaneously forming two clip members.
Figure 5:
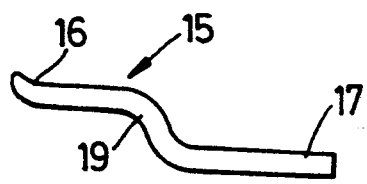
FIG. 5 is a side elevation of one clip member after bending of its tip.
Figure 6:
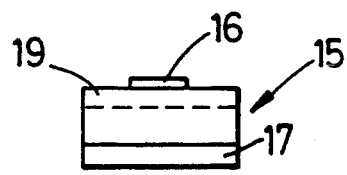
FIG. 6 is an end elevation from the right hand end of FIG. 5.

In FIG. 4 a pair of clip members 15 are formed simultaneously, each having a tip 16 engageable in one aperture 12 in the arched portion 11 of the bridge member 10 (see FIGS. 7 and 9) and each having a fixing portion 17 with a hole 18 for rotatably receiving a pedicle screw (again see FIG. 9).

FIGS. 7 and 9 show the tips 16 of the clip members 15 engaged in the apertures 12 in the arched portion 11 of the bridge member 10, the hole 18 in the fixing portion 17 of each clip member being in register with the corresponding hole 14 in the respective end portion 13 of the bridge member, and the portion 19 of each clip member 15 between its tip 16 and its fixing portion 17 is cranked so as to form with the junction 20 between the arched portion 11 and the respective end portion 13 of the bridge member 10 a pair of clamping parts for embracing a rod or rod-like portion 21 of a spinal fixation device.

The edges 22 of the arched portion 11 are concave in plan view to form a neck having its least width at the middle, to afford clearance with respect to adjacent spinous processes 23 (see FIG. 9).

The holes 14, 18 in the end portions 13 of the bridge member 10 and the fixing portions 17 of the clip members 15 respectively are formed and elongated by a ball cutter applied to the remote faces 24, 25 respectively and moved towards the arched portion 11 of the bridge member and away from the tips 16 of the clip portions respectively (as indicated by the arrows in FIG. 8).

FIG. 9 shows a "Hartshill Rectangle" 26 secured in place on the lower lumber spine by sub-laminar wires 27 at the junctions between the longer sides 21' and the bent shorter sides 28 of the rectangle, and pedicle screws 29—securing the assembly of the bridge member 10 and clip members 15 to the rectangle and to the spine, the screws 29 passing through the pedicle 30 and into the body of a vertebra 31.

We claim:

1. Pedicle engaging device comprising a bridge member having an arched middle portion with an aperture in each side of the arch, and a pair of generally coplanar end portions each with a hole for rotatably receiving a pedicle screw, a bend formed between the arched portion and each end portion; a pair of clip members each having a tip engageable in one aperture in the arched portion of the bridge member, and each having a fixing portion with a hole for rotatably receiving a pedicle screw, a bent portion formed between the tip and the fixing portion of each clip member; the hole in a clip member being in register with the hole in the respective end portion of the bridge member when the tip of the clip member is engaged in the respective aperture in the arched portion of the bridge member, and a pair of clamping parts being formed by the bent portion of each clip member and the corresponding bend in the bridge member, these clamping parts for embracing a rod or rod-like portion of a spinal fixation device.

2. Pedicle engaging device as in claim 1 formed of stainless steel strip.

3. Pedicle engaging device as in claim 1 wherein the holes in the end portions of the bridge member and in the fixing portions of the clip members are elongated in the lengthwise direction of the bridge member.

4. Pedicle engaging device comprising a bridge member having an arched middle portion with an aperture in each side of the arch, and a pair of generally coplanar end portions each with a hole for rotatably receiving a pedicle screw, a bend formed between the arched portion and each end portion; a pair of clip members each having a tip engageable in one aperture in the arched portion of the bridge member, and each having a fixing portion with a hole for rotatably receiving a pedicle screw, a bent portion formed between the tip and the fixing portion of each clip member; the hole in a clip member being in register with the hole in the respective end portion of the bridge member when the tip of the clip member is engaged in the respective aperture in the arched portion of the bridge member, and a pair of clamping parts being formed by the bent portion of each clip member and the corresponding bend in the bridge member, these clamping parts for embracing a rod or rod-like portion of a spinal fixation device wherein the width of the arched portion of the bridge member is reduced between the apertures for engagement by the tips of the clip members.

5. Pedicle engaging device as in claim 4 wherein the edge of the arched portion are concave as viewed from the arch to form a neck having its last width at the middle.

* * * * *